United States Patent
Lange

(10) Patent No.: US 7,326,249 B2
(45) Date of Patent: Feb. 5, 2008

(54) FLEXIBLE SPINE STABILIZATION SYSTEMS

(75) Inventor: Eric C. Lange, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 11/411,452

(22) Filed: Apr. 26, 2006

(65) Prior Publication Data

US 2006/0200140 A1 Sep. 7, 2006

Related U.S. Application Data

(63) Continuation of application No. 11/030,550, filed on Jan. 5, 2005, now Pat. No. 7,041,138, which is a continuation of application No. 10/682,695, filed on Oct. 9, 2003, now Pat. No. 6,852,128, which is a continuation of application No. 10/078,522, filed on Feb. 19, 2002, now Pat. No. 6,652,585.

(60) Provisional application No. 60/272,102, filed on Feb. 28, 2001.

(51) Int. Cl.
*A61F 2/44* (2006.01)
*A61B 17/56* (2006.01)

(52) U.S. Cl. .............. 623/17.11; 606/61
(58) Field of Classification Search .......... 623/17.11; 606/61
See application file for complete search history.

(56) References Cited

U.S. PATENT DOCUMENTS

| | | | |
|---|---|---|---|
| 3,463,158 A | 8/1969 | Schmitt et al. | 128/334 |
| 3,710,789 A | 1/1973 | Ersek | 128/92 |
| 4,570,623 A | 2/1986 | Ellison et al. | 128/92 |
| 4,610,688 A | 9/1986 | Silvestrini et al. | 623/1 |
| 4,665,951 A | 5/1987 | Ellis | 139/387 |
| 4,728,329 A | 3/1988 | Mansat | 623/13 |
| 4,743,260 A | 5/1988 | Burton | 623/17 |
| 4,755,183 A | 7/1988 | Kenna | 623/13 |
| 4,772,287 A | 9/1988 | Ray et al. | 623/17 |
| 4,820,305 A | 4/1989 | Harms et al. | 623/16 |
| 4,834,755 A | 5/1989 | Silvestrini et al. | 623/13 |
| 4,883,486 A | 11/1989 | Kapadia et al. | 623/13 |
| 4,904,260 A | 2/1990 | Ray et al. | 623/17 |
| 4,917,700 A | 4/1990 | Aikins | 623/13 |
| 4,955,911 A | 9/1990 | Frey et al. | 623/16 |
| 5,011,484 A | 4/1991 | Bréard | 606/61 |
| 5,084,051 A | 1/1992 | Törmälä et al. | 606/77 |
| 5,102,421 A | 4/1992 | Anspach, Jr. | 606/232 |
| 5,108,395 A | 4/1992 | Laurain | 606/61 |

(Continued)

FOREIGN PATENT DOCUMENTS

EP 0304305 2/1989

(Continued)

*Primary Examiner*—Cris Rodriguez
*Assistant Examiner*—Candice C Stokes
(74) *Attorney, Agent, or Firm*—Krieg DeVault LLP

(57) ABSTRACT

A spine stabilization system includes a flexible member attachable to a portion of the spinal column. The member includes components that are oriented and function similar to the natural fiber orientation of the anterior longitudinal ligament and annulus tissue. The use of components resist loading applied by extension and rotation of the spine, while the flexibility of the member does not subject it to the compressive loading of the spinal column segment to which it is attached.

20 Claims, 5 Drawing Sheets

U.S. PATENT DOCUMENTS

| | | | |
|---|---|---|---|
| 5,156,616 A | 10/1992 | Meadows et al. | 606/232 |
| 5,157,111 A | 10/1992 | Pachence | 530/356 |
| 5,171,273 A | 12/1992 | Silver et al. | 623/13 |
| 5,180,393 A | 1/1993 | Commarmond | 63/13 |
| 5,222,987 A | 6/1993 | Jones | 623/66 |
| 5,344,421 A | 9/1994 | Crook | 606/61 |
| 5,346,492 A | 9/1994 | Morgan | 606/60 |
| 5,376,118 A | 12/1994 | Kaplan et al. | 623/11 |
| 5,380,328 A | 1/1995 | Morgan | 606/70 |
| 5,397,359 A | 3/1995 | Mittelmeier et al. | 623/16 |
| 5,443,483 A | 8/1995 | Kirsch | 606/74 |
| 5,456,722 A | 10/1995 | McLeod et al. | 623/13 |
| 5,496,372 A | 3/1996 | Hamamoto et al. | 623/16 |
| 5,527,311 A | 6/1996 | Procter et al. | 606/61 |
| 5,540,964 A | 7/1996 | Mallen | 428/36.1 |
| 5,549,679 A | 8/1996 | Kuslich | 623/17 |
| 5,609,634 A | 3/1997 | Voydeville | 623/17 |
| 5,634,944 A | 6/1997 | Magram | 623/11 |
| 5,674,295 A | 10/1997 | Ray et al. | 623/17 |
| 5,681,310 A | 10/1997 | Yuan et al. | 606/61 |
| 5,711,960 A | 1/1998 | Shikinami | 424/426 |
| 5,721,049 A | 2/1998 | Marcolongo et al. | 428/370 |
| 5,824,093 A | 10/1998 | Ray et al. | 623/17 |
| 5,906,828 A | 5/1999 | Cima et al. | 424/423 |
| 6,022,376 A | 2/2000 | Assell et al. | 623/17 |
| 6,031,148 A | 2/2000 | Hayes et al. | 623/11 |
| 6,045,554 A | 4/2000 | Grooms et al. | 606/73 |
| 6,077,076 A | 6/2000 | Comfort | 433/173 |
| 6,093,205 A | 7/2000 | McLeod et al. | 623/17 |
| 6,113,640 A | 9/2000 | Törmälä et al. | 623/18 |
| 6,121,172 A | 9/2000 | Marcolongo et al. | 442/301 |
| 6,143,036 A | 11/2000 | Comfort | 623/23.54 |
| 6,162,537 A | 12/2000 | Martin et al. | 428/373 |
| 6,332,894 B1 | 12/2001 | Stalcup et al. | 623/17.11 |
| 6,652,585 B2 | 11/2003 | Lange | 623/17.11 |
| 6,852,128 B2 | 2/2005 | Lange | 623/17.11 |
| 7,041,138 B2 | 5/2006 | Lange | 623/17.11 |
| 2002/0123750 A1 | 9/2002 | Eisermann et al. | 606/69 |

FOREIGN PATENT DOCUMENTS

| | | |
|---|---|---|
| EP | 0353936 | 2/1990 |
| EP | 0507162 | 4/1991 |
| WO | WO 98/55053 | 12/1998 |
| WO | WO 99/47082 | 9/1999 |
| WO | WO 99/62439 | 12/1999 |
| WO | WO 00/59388 | 10/2000 |

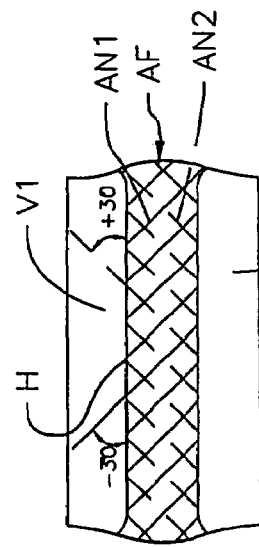
Fig. 3
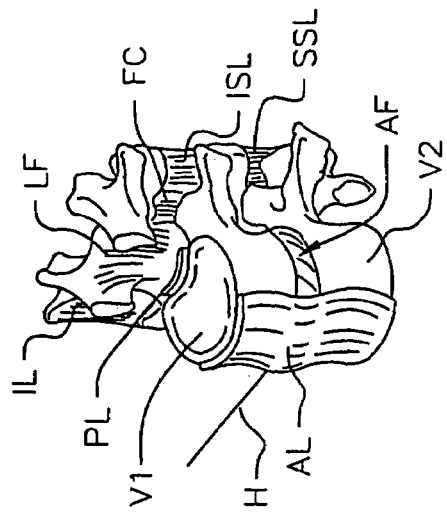
Fig. 4 (a)
Fig. 4 (b)
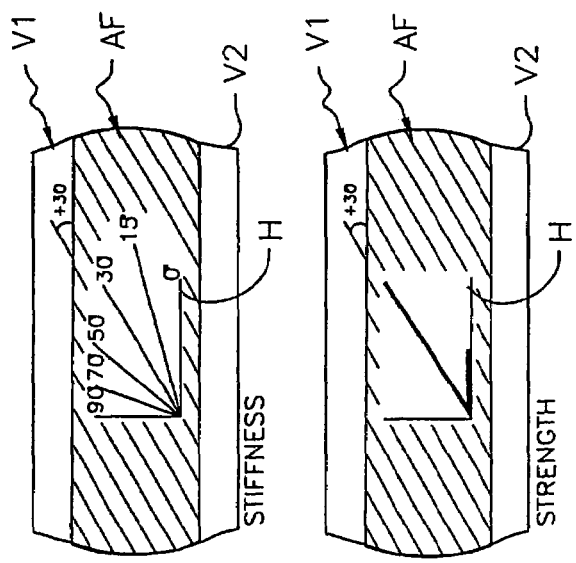
Fig. 5 (a)
Fig. 5 (b)
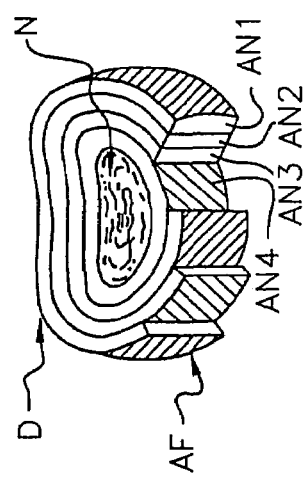

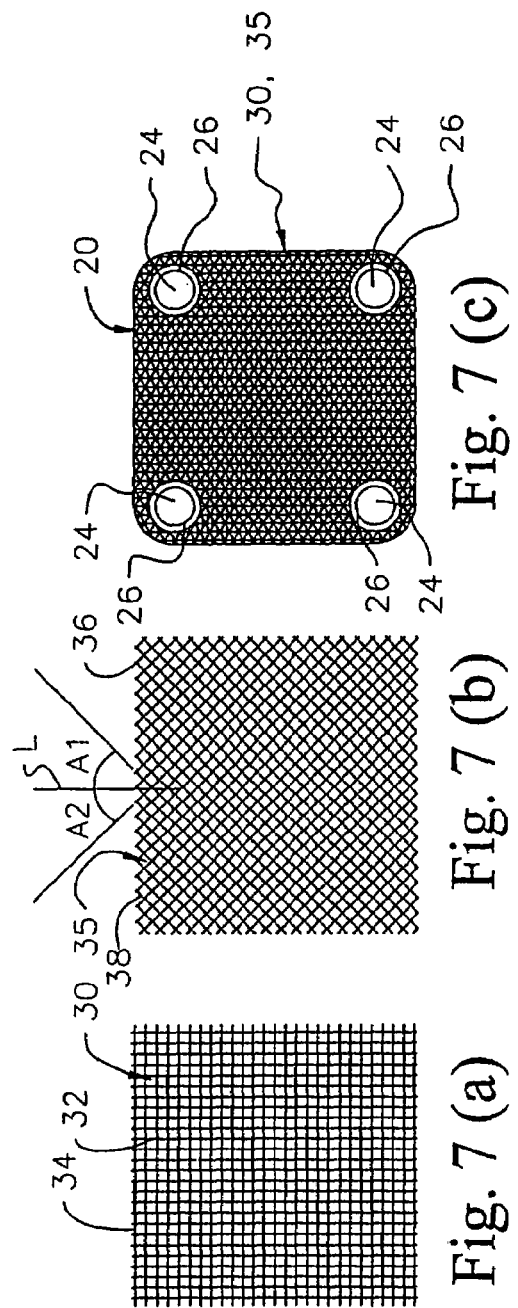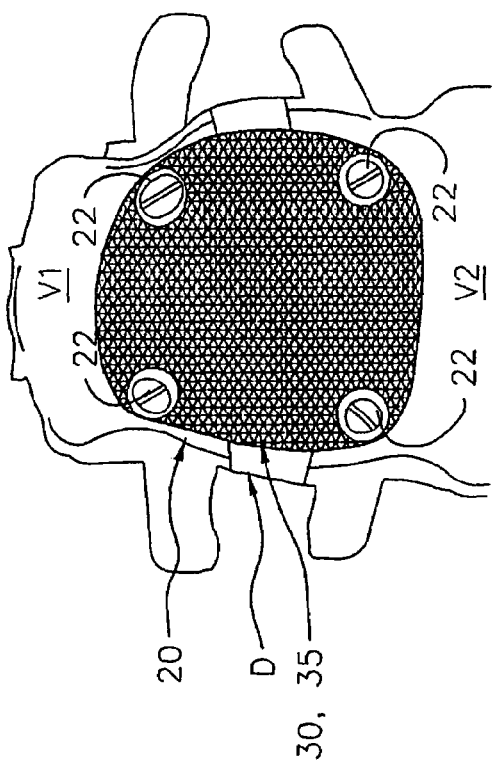

FLEXIBLE SPINE STABILIZATION SYSTEMS

CROSS-REFERENCE TO RELATED APPLICATION

The present application is a continuation of U.S. patent application Ser. No. 11/030,550 filed on Jan. 5, 2005, issuing as U.S. Pat. No. 7,041,138; which is a continuation of U.S. patent application Ser. No. 10/682,695 filed Oct. 9, 2003, and issued as U.S. Pat. No. 6,852,128; which is a continuation of U.S. patent application Ser. No. 10/078,522 filed on Feb. 19, 2002, and issued as U.S. Pat. No. 6,652,585; which claims the benefit of the filing date of Provisional Patent Application Ser. No. 60/272,102 filed on Feb. 28, 2001. Each of the referenced applications is incorporated herein by reference in its entirety.

BACKGROUND

The present invention relates to orthopedic implants, and more particularly, to flexible spinal stabilization systems.

Interbody fusion device, artificial discs, interbody spacers and other devices have been inserted in a spinal disc space or engaged to a vertebral body. For example, as shown in FIG. 1, a pair of interbody fusion devices I1 and I2 are inserted into an intradiscal space between the L5 and S1 levels of the spinal column. Aorta A1 and vena cava A2 along with other tissue and vasculature also extend along the anterior aspect of the spinal column. As shown in FIG. 2, the anterior longitudinal ligament AL extends along the anterior portion of the disc space. The disc space is surrounded by annulus fibrosus or annulus fibers AF. Insertion of implants I1 and I2 into the disc space can be facilitated by the removal of all or a portion of the anterior longitudinal ligament AL and the annulus fibers AF.

In order to stabilize the spinal column, it is known to secure a rigid metal construct to each of the vertebral bodies on either side of the spinal disc space after inserting devices or performing surgical procedures in the disc space or on the vertebral bodies. For example, a rigid metal plate can be placed along the anterior aspect of the vertebrae and secured to the L5 and S1 levels after insertion of implants I1 and I2 into the disc space therebetween. In another example, a rigid rod or plate can be secured to the posterior portions of vertebrae V1 and V2 after anterior insertion of implants I1 and I2.

While rigid metal constructs provide adequate load resistance, there can be drawbacks, such as the intrusion of the construct into the adjacent tissue and vasculature, stress shielding, multiple surgeries for installation, and fatigue. What are needed are systems that do not require posterior hardware to support the spinal column or rigid anterior, antero-lateral, or lateral plates and constructs. The systems should be resistant to fatigue, stress shielding and tensile and rotational loads that are typically applied to the spinal column. The present invention is directed toward meeting these needs, among others.

SUMMARY

The present invention is directed to spine stabilization systems that are flexible and include components that replicate, substitute and/or augment the natural fiber orientation of the anterior longitudinal ligament and annulus tissue. The components resist loading applied by extension and rotation of the spine, while the flexibility of the components does not subject them to the compressive loading of the spinal column segment to which it is secured.

DESCRIPTION OF THE FIGURES

FIG. 3 is a perspective view a spinal column segment with its associated ligaments.

FIGS. 4(a) and 4(b) illustrate various features of a spinal disc space.

FIGS. 5(a) and 5(b) illustrate various structural properties of the annulus fibrosous.

FIG. 6 is a flexible spine stabilization system according to one embodiment secured to a spinal column segment.

FIGS. 7(a) through 7(c) show various components of the system of FIG. 6.

DESCRIPTION OF THE ILLUSTRATED EMBODIMENTS

Figure 1:
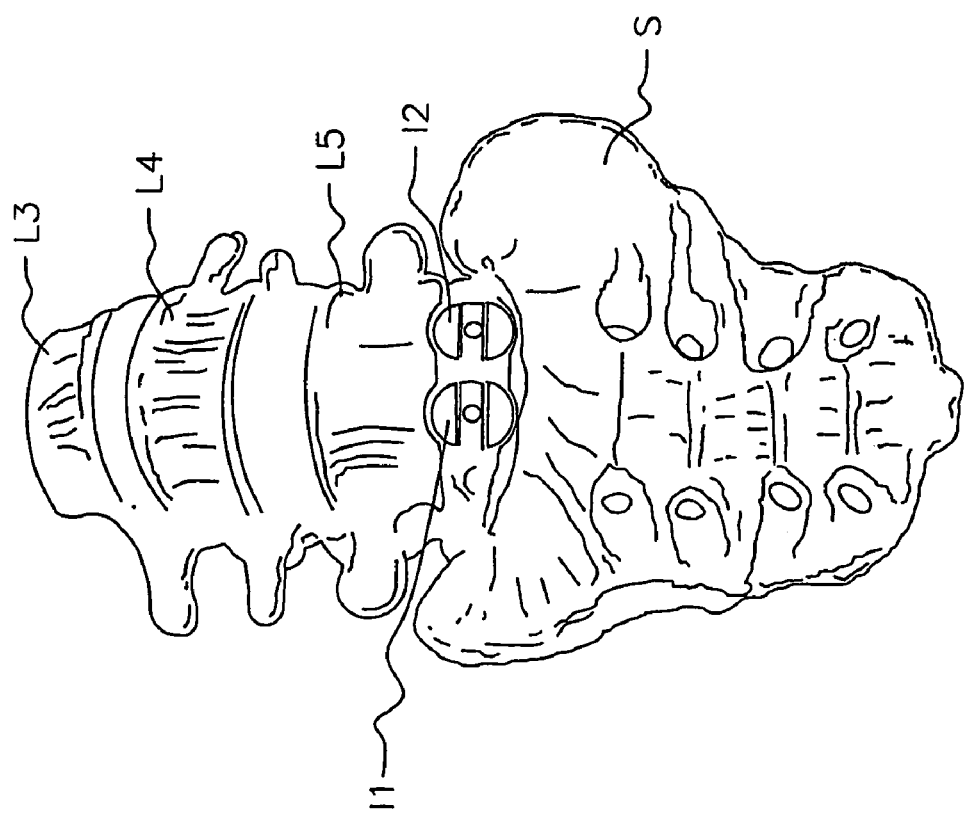
FIG. 1 is an elevational view of a spinal column segment having a pair of interbody fusion devices inserted into a disc space.

For the purposes of promoting an understanding of the principles of the invention, reference will now be made to the illustrated embodiments and specific language will be used to describe the same. It will nevertheless be understood that no limitation of the scope of the invention is thereby intended. Any such alterations and further modifications of the invention, and any such further applications of the principles of the invention as illustrated herein are contemplated as would normally occur to one skilled in the art to which the invention relates.

The present invention is directed to flexible spine stabilization systems for placement on the anterior aspect of the vertebrae of a spinal column segment. It is contemplated the systems may also be placed on the antero-lateral aspect or the lateral aspect of the vertebrae. It is also contemplates that the systems can extend across one or more vertebral levels. The systems are configured to replicate, substitute and/or augment the structure and function of the natural occurring fibers that protect the intervertebral disc space. It is further contemplated that the systems can be used in lieu of the placement of a rigid anterior plate across one or more disc spaces after insertion of an interbody fusion device into the disc space. It is also contemplated that the systems can be used in non-interbody fusion procedures.

The spine stabilization systems include a member having a first set of one or more components oriented generally in the direction of the annulus fibers, and a second set of components oriented generally in the direction of the fibers of the anterior longitudinal ligament. The use of components having such orientations provides resistance to loading applied by extension, lateral bending, and rotation of the spine. The flexibility of the member does not subject it to stress shielding caused by the compressive loading of the spinal column segment to which it is secured. Thus, the spine stabilization systems of the present invention replicate, augment and/or substitute the load resistant properties capabilities of the annulus fibers and anterior longitudinal ligament.

Further description of flexible spinal stabilization systems is provided after the following discussion of the anatomical features of the annulus and anterior longitudinal ligament. Referring now to FIG. 3, a spinal column segment including an upper vertebra V1 and lower vertebra V2 is illustrated. The spinal column segment includes anterior longitudinal ligament AL extending along the anterior aspects of vertebra V1 and vertebra V2 and across the intervertebral disc space between vertebrae V1 and V2. The nucleus of the disc space is protected by annulus fibers AF. The spinal column segment further includes posterior longitudinal ligament PL, intertransverse ligament IL, facet capsular ligament FC, interspinous ligament ISL, superspinous ligament SSL, and ligamentum flavum LF. The spine is designed in such a way that when the functional spinal unit is subjected to different complex force and torque vectors, the individual ligaments provide tensile resistance to external loads by developing tension. When a surgical procedure interrupts or removes a portion of these ligaments, the ability of the spinal unit to resist these complex force and torque vectors is compromised.

The anterior longitudinal ligament AL is an uni-axial structure, and is most effective in carrying loads along the direction in which the fibers run. The anterior longitudinal ligament AL has a fibrous tissue structure that arises from the anterior aspect of the basioccipital and is attached to the atlas and the anterior surfaces of all vertebrae, down to and including a part of the sacrum. It is firmly attached to the edges of the vertebral bodies, but is less firmly affixed to the annulus fibers AF. The width of the anterior longitudinal ligament AL diminishes at the level of disc and is narrower and thicker in the thoracic region of the spine. The fibers of the anterior longitudinal ligament run along the length of the spinal column in the direction of the central spinal column axis and transverse to axial plane H. The fibers of the anterior longitudinal ligament AL are much like rubber bands in that they readily resist tensile forces, but buckle when subjected to compressive forces.

Figure 2:
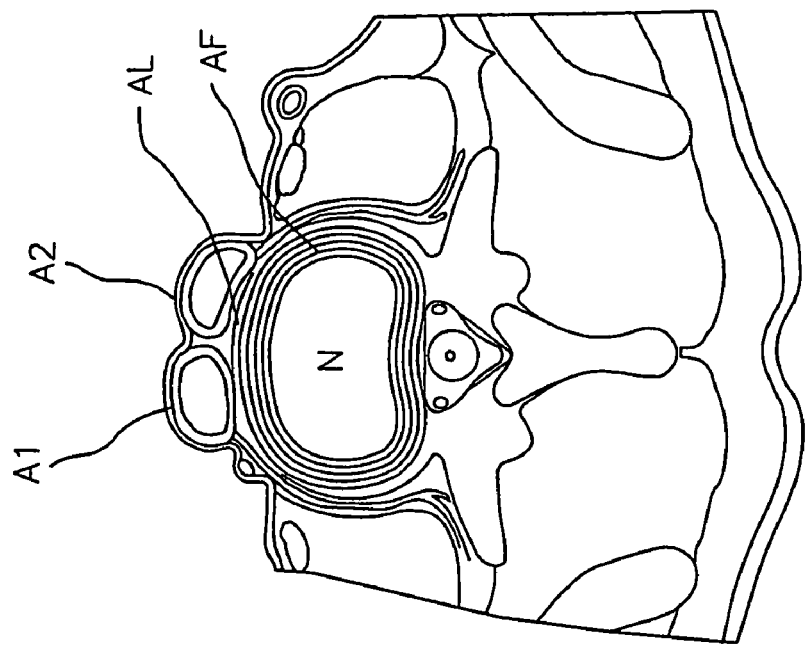
FIG. 2 is a plan view of a disc space of a spinal column segment and the surrounding tissue and vasculature.

Referring now to FIGS. 4(a) and 4(b), further properties of the spinal disc space D will be discussed. The nucleus pulposus N of the disc space is surrounded by the annulus fibrosus AF. The annulus fibrosus AF includes a number of concentric laminated bands, designated as annulus laminates AN1, AN2, AN3, and AN4 as shown in FIG. 4(a). As shown further in FIG. 4(b), these annulus laminates AN have fibers oriented either +30 degrees or −30 degrees with respect to axial plane H of the spinal column. Stated another way, the AN fibers are oriented about +60 degrees or about −60 degrees with respect to the fibers of the anterior longitudinal ligament AL. The fibers of the adjacent annulus laminates AN are non-orthogonal with respect to axial plane H and to one another, forming a criss-cross pattern as shown by AN1 and AN2 of FIG. 2(b). When interbody fusion devices or other implants are inserted between the vertebrae, or when the disc space is access for surgical procedures, the resection, removal and other cutting required of the annulus laminates AN and anterior longitudinal ligament AL disrupts fiber orientation and continuity.

Referring now to FIGS. 5(a) and 5(b), the tensile properties and strength properties of the annulus fibrosis will now be discussed. The annulus fibers AF resist tensile forces and torque or rotational forces applied to the spinal column segment. In FIG. 5(a), the tensile stiffness of the annulus AF in different directions is shown. The stiffness of annulus fibrosus AF is highest along a direction oriented 15 degrees with respect to axial plane H. In FIG. 5(b), the strength of the annulus AF has been found to be greatest along a direction oriented 30 degree with respect to horizontal axis H extending through the disc space. It has further been found that the strength of the annulus AF is three times greater along this 30 degree axis as compared to the strength along axial plane H.

Referring now to FIG. 6, a spine stabilization system 20 is illustrated. System 20 is secured to vertebra V1 and vertebra V2 and extends across the disc space D. It is contemplated that one or more interbody fusion devices, interbody spacers, artificial discs or other implant can be inserted into disc space D in a procedure prior to attachment of system 20 to vertebrae V1 and V2. It is also contemplated that a surgical procedure can be performed in or on disc space D such as, for example, removal of discal material to repair a herniated disc. In such procedures, the excision or disruption to the annulus fibrosus AF and the anterior longitudinal ligament AL compromises the ability of these spinal structures to resist extension, torsion, and lateral bending of the spinal column. System 20 can restore this ability and can cover the entry made through the annulus fibrosis AF and anterior longitudinal ligament AL, preventing devices inserted into the disc space from backing out or protruding through the created opening.

System 20 includes diagonal components and vertical components. The diagonal components can be oriented in the range of 15 degrees to 60 degrees with respect to axial plane H when the devices are secured to the vertebrae. The vertical components extend generally perpendicular to axial plane H. Stated another way, a first set of diagonal components extends at an angle A1 in the range of +30 degrees to +75 degrees relative to the vertical components, and a second set of diagonal components extends transverse to the first set and at an angle A2 in the range of −30 degrees to −75 degrees relative to the vertical components. In another form, the first set of diagonal components extends at an angle A1 in the range of +45 degrees to +60 degrees relative to the vertical components, and the second set of diagonal components extends transverse to the first set and at an angle A2 in the range of −45 degrees to −60 degrees relative to the vertical components. In a further form, the first set of diagonal components extends at an angle A1 of about +60 degrees relative to the vertical components, and the second set of diagonal components extends transverse to the first set and at an angle A2 of about −60 degrees relative to the vertical components.

Referring now to FIGS. 7(a) through 7(c), there are shown various components of system 20. System 20 includes a member extending between the first and second vertebrae V1 and V2. The member includes a first layer 30 which has a number of vertically oriented components 34 and a number of horizontally oriented components 32. Components 32, 34 are interwoven or otherwise attached to form a grid-like or mesh pattern having a number of square apertures therethrough. The member further includes a second layer 35 as shown in FIG. 7(b) having a number of first diagonal components 36 and a number of second diagonal components 38. Diagonal components 36 and 38 are interwoven or otherwise attached to form a grid-like or mesh pattern having a number of diamond-shaped apertures. Each layer 30, 35 is flexible in compression yet inelastic or substantially inelastic to resist tensile loading.

The individual components 32, 34, 36, 38 of each layer can be made from a small diameter or cross-section wire, fiber, rod, strand or other elongated component. As shown in FIG. 7(c), first layer 30 is placed on top of second layer 35 and secured thereto via grommets 26. Other securement devices and techniques are also contemplated, including, for example, other fasteners such as rivets, clamps, cables, sutures, staples, and hooks; and chemical/thermal bonding, such as welding or adhesives. Other embodiments contemplate that layers 30, 35 are not engaged to one another, but rather simply placed on top of one another when secured to the spinal column.

A number of openings 24 are formed through the layers to accommodate fasteners 22. In the illustrated embodiment, four such openings are formed, with one opening positioned adjacent each corner. Eyelets or grommets 26 extend around each hole 24. As shown in FIG. 6, bone engaging fasteners 22 can be placed through corresponding ones of the holes 24 to secure layers 30, 35 to vertebrae V1 and V2. The corners of layers 30, 35 can be rounded to provide gradual transitions between the vertical and horizontal edges thereof. Other embodiments contemplate one opening 24 at each vertebra, and further embodiments contemplate more than two openings 24 at each vertebra. Other embodiments also contemplate that no openings are provided, but rather the fasteners extend directly through the layers of material.

The vertically extending components 34 of first layer 30 are oriented and function in a manner similar to the longitudinal fibers of the anterior longitudinal ligament AL. Diagonal components 36, 38 of second layer 35 are non-orthogonally oriented with respect to the vertical components 34, and are oriented and function similar to annulus fibers AF. Thus, system 20 replaces, substitutes, and/or augments the function of the naturally occurring fibers of the anterior longitudinal ligament AL and the annulus fibrosis AF. The orientation of the components of system 20 are such that forces caused by extension, rotation, and lateral bending of the spinal column are resisted in a manner the same as or similar to the natural occurring anatomical structures provided to resist such forces.

Figure 8A:
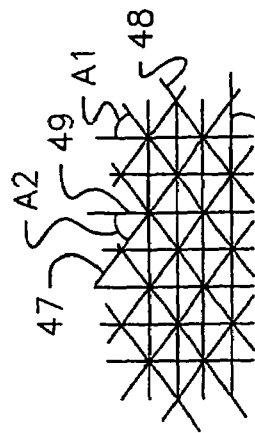
FIG. 8a is an enlarged detail view of a portion of the system of FIG. 8.
Figure 8:
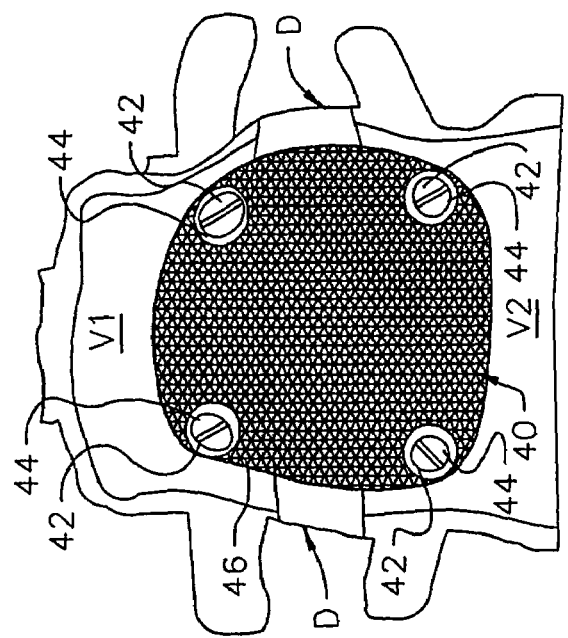
FIG. 8 is an elevational view of another embodiment flexible spine stabilization system secured to a spinal column segment.

Referring to FIGS. 8 and 8a, there is provided a spine stabilization system 40 having a layer 46. Layer 46 includes a number of interwoven components that include at least longitudinally and diagonally oriented components. In the illustrated embodiment, there are provided first diagonal components 47, second diagonal components 48, vertical components 49, and horizontal components 45. The first and second diagonal components 47, 48 are oriented and function similar to the fibers of the annulus fibrosis AF, and the vertical components 49 are oriented and function similar to the anterior longitudinal ligament AL. Small apertures are provided through layer 46 between its components. Eyelets or grommets 44 each surround a corresponding one of the holes provided through layer 46. Bone engaging fasteners 42 extend through these holes to attach system 40 to vertebra V1 and vertebra V2.

Figure 9:
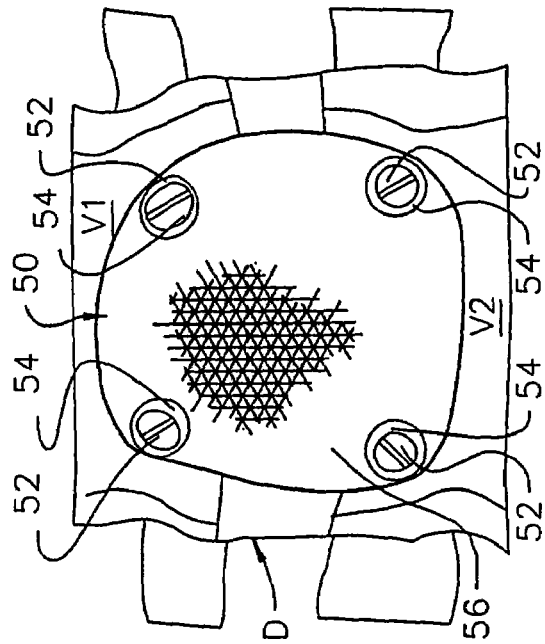
FIG. 9 is elevational view of yet another embodiment flexible spine stabilization system secured to a spinal column segment.

Referring now to FIG. 9, there is shown another embodiment spine stabilization system 50. The components of system 50 are diagonally and vertically oriented to replicate the orientation of the fibers of the anterior longitudinal ligament AL and annulus fibers AF. System 50 includes a member formed by a layer 56 made from components interwoven such that there are no apertures through layer 56, providing a substantially solid wall across disc space D. Layer 56 includes a number of holes formed therethrough surrounded by grommets or eyelets 54. Fasteners 52 extend through the holes in order to secure the flexible system 50 to vertebra V1 and V2 across the annulus fibrosis AF.

Figure 10:
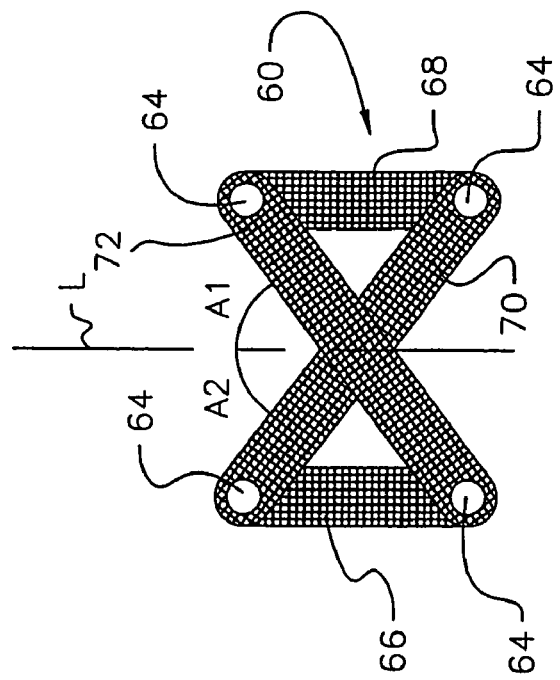
FIG. 10(a) is an elevational view of a further embodiment flexible spine stabilization system.
FIG. 10(b) is the system of FIG. 10(a) secured to a spinal column segment.
Figure 10:
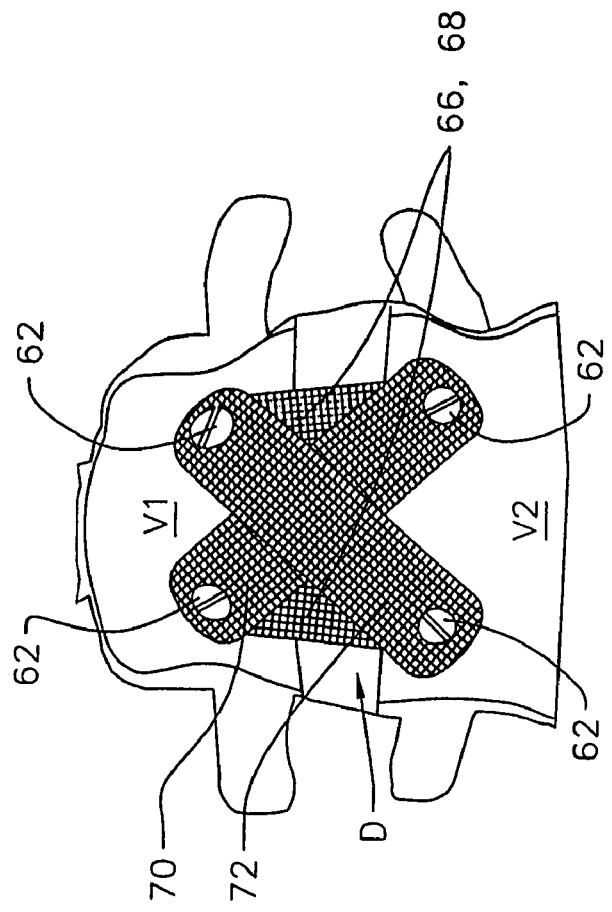

Referring now to FIG. 10(a), another embodiment spine stabilization system 60 is illustrated. System 60 includes member having a first vertical component 66 and a second vertical component 68. Vertical components 66 and 68 are interconnected by a first diagonal component 70 and a second diagonal component 72. As shown in FIG. 10(b), first diagonal component 70 extends from a right lateral side of vertebral body V2 across the sagittal plane L to a left lateral side of vertebral body V1. Second diagonal component 72 extends from the left lateral side of vertebral body V2 across thee sagittal plane L to the right lateral side of vertebral body V1. The first vertical component 66 extends from a left lateral side of vertebral body V2 to the left lateral side of vertebral body V1 offset to one side of sagittal plane L. Second vertical component 68 extends from the right lateral side of vertebral body V2 to the right lateral side of vertebral body V1 offset to the other side of sagittal plane L. In each corner of system 60 there is formed a hole 64 for receiving a fastener 62 to attach system 60 to vertebrae V1 and V2.

The vertically oriented components 66, 68 are oriented to replace, substitute and/or augment the structure function of the anterior longitudinal ligament AL and resist at least extension forces applied to the spinal column segment. The diagonal components 70, 72 are non-orthogonally oriented with respect to the vertically oriented components 66, 68 and resist at least rotational and torque forces on the spinal column segment. Thus, diagonal components 70, 72 are oriented and function similar to the fibers of the annulus fibrosis AF.

The components of the flexible spinal stabilization systems can be made from one or a combination of metal material, polymeric material, ceramic material, shape memory material, and composites thereof. The components of the systems can also be coated or impregnated with anti-adhesive material that will prevent tissue and vasculature from attaching thereto. The components of the systems can be provided in multiple layers each including one or more components with the desired orientation and placed one on top of the other, or the components can be provided in a single interwoven layer that includes the desired component orientation.

In one specific embodiment, the components are made from metal wire mesh of suitable tensile strength and which is not subject to substantial creep deformation or in vitro degradation. It is contemplated that the wire can be made from stainless steel, cobalt-chrome alloy, titanium, titanium alloy, or nickel-titanium, among others.

In another specific embodiment, the components are made from a soft fiber material. Soft fiber material can include polymeric material, such as SPECTRA fiber, nylon, carbon fiber and polyethylene, among others. Examples of suitable metal polymers include DACRON and GORE-TEX. One advantage provided by a soft fiber design is that the risk of tissue and vascular injury is further mitigated by reducing the abrasive qualities of the component material. A further advantage is that the components fibers can be radiolucent, allowing radiographic imaging for assessment and monitoring of the disc space and any implant, fusion devices, or artificial disc inserted therein. Another advantage is that some polymeric materials, such as spectra fiber, can be stronger than metals and less susceptible to fatigue or creep.

While the invention has been illustrated and described in detail in the drawings and foregoing description, the same is to be considered as illustrative and not restrictive in character, it being understood that the preferred embodiments have been shown and described, and that all changes and modifications that come within the spirit of the invention are desired to be protected.

What is claimed is:

1. A spinal stabilization device, comprising:
a flexible member having opposite edges spaced from one another along an axis with a length sized for attachment between first and second vertebrae, said flexible member including a mesh pattern comprising a first layer including a number of square shaped apertures along the axis extending through said first layer and a second layer including a number of diamond shaped apertures along the axis extending through said second layer, wherein said diamond shaped apertures include sides obliquely oriented to said axis of said flexible member and said square shaped apertures include sides paralleling said axis of said flexible member.

2. The device of claim 1, wherein said first layer includes a number of vertically oriented components paralleling said axis and a number of horizontally oriented components attached to said vertically oriented components and said second layer includes a number of first and second diagonal components extending transversely to and attached to one another, said first and second diagonal components being obliquely oriented to said axis.

3. The device of claim 2, wherein said vertically and horizontally oriented components are interwoven with one another and said diagonally oriented components are interwoven with one another.

4. The device of claim 2, wherein said first layer and said second layer are placed one on top of the other for attachment to the adjacent vertebrae.

5. The device of claim 1, wherein said flexible member is flexible in compression and substantially inelastic in tension.

6. The device of claim 1, further comprising grommets positioned adjacent said opposite ends for securing said first and second layers to one another, said grommets each defining a hole for receiving a fastener.

7. The device of claim 1, wherein said opposite edges define horizontal edges of said mesh pattern and said mesh pattern further includes vertical edges extending between said horizontal edges, said mesh pattern further including rounded corners transitioning between said vertical and horizontal edges.

8. A spinal stabilization device, comprising:
a flexible member having opposite ends spaced from one another along an axis with a length sized for attachment between first and second vertebrae, said flexible member including a mesh pattern comprising a single layer including a number of openings extending therethrough between opposing surfaces, at least a portion of said number of openings being defined by at least one of a plurality of vertical components of said mesh pattern extending along said axis and at least one of a plurality of first diagonal components of said mesh pattern that are obliquely oriented to said axis and said vertical components.

9. The device of claim 8, wherein said mesh pattern further comprises a plurality of second diagonal components obliquely oriented to said axis and transversely oriented to said plurality of first diagonal components, wherein at least one of said first and second diagonal components extends along a side of each of said number of openings.

10. The device of claim 9, wherein said mesh pattern further comprises a plurality of horizontal components extending along a side of each of said number of openings.

11. The device of claim 10, wherein said vertical components, said first and second diagonal components and said horizontal components are interwoven.

12. The device of claim 8, further comprising at least one grommet positioned adjacent each of said opposite ends, said grommets each defining a hole through said mesh pattern for receiving a fastener.

13. The device of claim 8, wherein said vertical components and said horizontal components are made from wire.

14. The device of claim 8, wherein said layer includes anti-adhesive material to prevent tissue attachment thereto.

15. A device for spinal stabilization, comprising:
a first member extending along a longitudinal axis between opposite first and second ends, said first and second ends being spaced by a length sized for attachment to first and second vertebrae;
a second member extending along said longitudinal axis between opposite first and second ends, said first and second ends being spaced by a length sized for attachment to first and second vertebrae, wherein said first and second members are spaced from one another on opposite sides of said longitudinal axis;
at least one diagonal member obliquely oriented to said longitudinal axis and extending between said first end of said first member and said second end of said second member; and
a first fastener extending through said diagonal member and said first end of said first member and a second fastener extending through said diagonal member and said second end of said second member.

16. The device of claim 15, further comprising at least one second diagonal member obliquely oriented to said longitudinal axis and extending between said second end of said first member and said first end of said second member.

17. The device of claim 16, further comprising a third fastener extending through said second diagonal member and said second end of said first member and a fourth fastener extending through said second diagonal member and said first end of said second member.

18. The device of claim 15, wherein said first member, said second member and said at least one diagonal member are comprised of a soft fabric material.

19. The device of claim 18, wherein said soft fabric material is a polymeric material.

20. The device of claim 15, wherein said first member, said second member and said at least one diagonal member are flexible in compression and inelastic in tension.

* * * * *